United States Patent
Popp et al.

(10) Patent No.: US 8,491,556 B2
(45) Date of Patent: Jul. 23, 2013

(54) ABSORBENT GARMENTS WITH MULTIPART LINER HAVING VARIED STRETCH PROPERTIES

(75) Inventors: Robert L. Popp, Hortonville, WI (US); Lawrence H. Sawyer, Neenah, WI (US); Joseph D. Coenen, Kaukauna, WI (US); Christopher P. Olson, Neenah, WI (US); Michael J. Faulks, Neenah, WI (US); James M. Carr, Kaukauna, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1731 days.

(21) Appl. No.: 11/305,182

(22) Filed: Dec. 15, 2005

(65) Prior Publication Data

US 2007/0142812 A1    Jun. 21, 2007

(51) Int. Cl.
*A61F 13/15* (2006.01)

(52) U.S. Cl.
USPC ............ 604/385.24; 604/385.22; 604/385.25; 604/385.28

(58) Field of Classification Search
USPC .............. 604/385.24, 385.22, 385.25, 385.28
See application file for complete search history.

(56) References Cited

U.S. PATENT DOCUMENTS

| | | | |
|---|---|---|---|
| 2,931,361 A | 4/1960 | Sostrin | |
| 3,849,241 A | 11/1974 | Butin et al. | |
| 3,978,861 A | 9/1976 | Schaar | |
| 4,036,233 A | 7/1977 | Kozak | |
| 4,050,462 A | 9/1977 | Woon et al. | |
| 4,100,324 A | 7/1978 | Anderson et al. | |
| 4,205,679 A | 6/1980 | Repke et al. | |
| 4,381,781 A | 5/1983 | Sciaraffa et al. | |
| 4,500,316 A | 2/1985 | Damico | |
| 4,560,372 A | 12/1985 | Pieniak | |
| 4,573,986 A | 3/1986 | Minetola et al. | |
| 4,657,802 A | 4/1987 | Morman | |
| 4,663,220 A | 5/1987 | Wisneski et al. | |
| 4,701,171 A | 10/1987 | Boland et al. | |
| 4,704,114 A | 11/1987 | Wilson et al. | |

(Continued)

FOREIGN PATENT DOCUMENTS

| | | |
|---|---|---|
| EP | 0 556 749 A1 | 8/1993 |
| EP | 0 957 868 B1 | 2/2003 |

(Continued)

OTHER PUBLICATIONS

Patent Cooperation Treaty Search Report from the International Search Authority, International Application No. PCT/US 2006/046691 dated Apr. 16, 2007.

(Continued)

*Primary Examiner* — Jacqueline F. Stephens
(74) *Attorney, Agent, or Firm* — Luke D. Kohtala

(57) ABSTRACT

Absorbent articles with stretch direction properties are disclosed, having at least three stretch zones. A first edge zone and a second edge zone are separated by a middle zone. The middle zone, which may the same length as each edge zone, has different stretch-direction characteristics than the edge zones. The middle zone may stretch in a single direction, whereas the edge zones may stretch in a different single direction or in bi- or multi-axial directions. The flaps may be created from the edge zones. Through this construction, the absorbent article exhibits improved fit and appearance.

23 Claims, 6 Drawing Sheets

U.S. PATENT DOCUMENTS

| | | | |
|---|---|---|---|
| 4,704,116 A | 11/1987 | Enloe |
| 4,710,187 A | 12/1987 | Boland et al. |
| 4,720,415 A | 1/1988 | Vander Wielen et al. |
| 4,731,066 A | 3/1988 | Korpman |
| 4,747,846 A | 5/1988 | Boland et al. |
| 4,752,349 A | 6/1988 | Gebel |
| 4,753,646 A | 6/1988 | Enloe |
| 4,756,709 A | 7/1988 | Stevens |
| 4,808,176 A | 2/1989 | Kielpikowski |
| 4,826,499 A | 5/1989 | Ahr |
| 4,834,736 A | 5/1989 | Boland et al. |
| 4,846,823 A | 7/1989 | Enloe |
| 4,854,995 A | 8/1989 | Kasper et al. |
| 4,857,067 A | 8/1989 | Wood et al. |
| 4,865,597 A | 9/1989 | Mason, Jr. et al. |
| 4,874,451 A | 10/1989 | Boger et al. |
| 4,892,536 A | 1/1990 | Desmarais et al. |
| 4,911,702 A | 3/1990 | O'Leary et al. |
| 4,935,021 A | 6/1990 | Huffman et al. |
| 4,938,753 A | 7/1990 | Van Gompel et al. |
| 4,938,755 A | 7/1990 | Foreman |
| 4,940,464 A | 7/1990 | Van Gompel et al. |
| 4,990,147 A | 2/1991 | Freeland |
| 4,998,929 A | 3/1991 | Bjorksund et al. |
| 5,026,364 A | 6/1991 | Robertson |
| 5,037,416 A | 8/1991 | Allen et al. |
| 5,046,272 A | 9/1991 | Vogt et al. |
| 5,104,116 A | 4/1992 | Pohjola |
| 5,114,781 A | 5/1992 | Morman |
| 5,116,662 A | 5/1992 | Morman |
| 5,151,092 A | 9/1992 | Buell et al. |
| 5,188,626 A | 2/1993 | Toyoda et al. |
| 5,224,405 A | 7/1993 | Pohjola |
| 5,226,992 A | 7/1993 | Morman |
| 5,242,436 A | 9/1993 | Weil et al. |
| 5,256,405 A | 10/1993 | Chappell et al. |
| 5,269,775 A | 12/1993 | Freeland et al. |
| 5,284,703 A | 2/1994 | Everhart et al. |
| 5,340,424 A | 8/1994 | Matsushita |
| 5,350,624 A | 9/1994 | Georger et al. |
| 5,368,584 A | 11/1994 | Clear et al. |
| 5,370,634 A | 12/1994 | Ando et al. |
| 5,383,871 A | 1/1995 | Carlin et al. |
| 5,397,316 A | 3/1995 | Lavon et al. |
| 5,397,317 A | 3/1995 | Thomas |
| 5,455,992 A | 10/1995 | Kurschatke et al. |
| 5,486,166 A | 1/1996 | Bishop et al. |
| 5,490,846 A | 2/1996 | Ellis et al. |
| 5,503,076 A | 4/1996 | Yeo |
| 5,554,143 A | 9/1996 | Roe et al. |
| 5,554,145 A | 9/1996 | Roe et al. |
| 5,611,790 A | 3/1997 | Osborn, III et al. |
| 5,624,422 A | 4/1997 | Allen |
| 5,634,916 A | 6/1997 | Lavon et al. |
| 5,643,242 A | 7/1997 | Lavon et al. |
| 5,645,542 A | 7/1997 | Anjur et al. |
| 5,658,269 A | 8/1997 | Osborn, III et al. |
| 5,669,897 A | 9/1997 | Lavon et al. |
| 5,690,627 A | 11/1997 | Clear et al. |
| 5,695,868 A | 12/1997 | McCormack |
| 5,766,389 A | 6/1998 | Brandon et al. |
| 5,804,021 A | 9/1998 | Abuto et al. |
| 5,817,086 A | 10/1998 | Kling |
| 5,820,973 A | 10/1998 | Dodge, II et al. |
| 5,843,056 A | 12/1998 | Good et al. |
| 5,846,232 A | 12/1998 | Serbiak et al. |
| 5,873,868 A | 2/1999 | Nakahata |
| 5,883,028 A | 3/1999 | Morman et al. |
| 5,897,545 A | 4/1999 | Kline et al. |
| 5,899,895 A | 5/1999 | Robles et al. |
| 5,914,184 A | 6/1999 | Morman |
| 5,928,211 A | 7/1999 | Gustafsson et al. |
| 5,947,947 A | 9/1999 | Tanzer et al. |
| 5,957,907 A | 9/1999 | Sauer |
| 5,957,908 A | 9/1999 | Kline et al. |
| 5,964,743 A | 10/1999 | Abuto et al. |
| 5,997,521 A | 12/1999 | Robles et al. |
| 5,997,981 A | 12/1999 | McCormack et al. |
| 6,004,306 A | 12/1999 | Robles et al. |
| 6,049,915 A | 4/2000 | Malowaniec |
| 6,093,870 A | 7/2000 | Carlsson |
| 6,103,953 A | 8/2000 | Cree et al. |
| 6,113,717 A | 9/2000 | Vogt et al. |
| 6,120,485 A | 9/2000 | Gustafsson et al. |
| 6,129,720 A | 10/2000 | Blenke et al. |
| 6,132,411 A | 10/2000 | Huber et al. |
| 6,149,638 A | 11/2000 | Vogt et al. |
| 6,149,934 A | 11/2000 | Krzysik et al. |
| 6,160,197 A | 12/2000 | Lassen et al. |
| 6,174,303 B1 | 1/2001 | Suprise et al. |
| 6,193,701 B1 | 2/2001 | Van Gompel et al. |
| 6,217,563 B1 | 4/2001 | Van Gompel et al. |
| 6,231,557 B1 | 5/2001 | Krautkramer et al. |
| 6,262,331 B1 | 7/2001 | Nakahata et al. |
| 6,264,639 B1 | 7/2001 | Sauer |
| 6,264,641 B1 | 7/2001 | Van Gompel et al. |
| 6,312,786 B1 | 11/2001 | Schwinn |
| 6,362,389 B1 | 3/2002 | McDowall et al. |
| 6,383,431 B1 | 5/2002 | Dobrin et al. |
| 6,409,711 B1 | 6/2002 | Jönbrink |
| 6,413,247 B1 | 7/2002 | Carlucci et al. |
| 6,461,338 B1 | 10/2002 | Shimoe et al. |
| 6,482,191 B1 | 11/2002 | Roe et al. |
| 6,521,811 B1 | 2/2003 | Lassen et al. |
| 6,552,245 B1 | 4/2003 | Roessler et al. |
| 6,570,056 B1 | 5/2003 | Tanzer et al. |
| 6,572,598 B1 | 6/2003 | Ashton et al. |
| 6,582,414 B1 | 6/2003 | Richardson |
| 6,595,975 B2 | 7/2003 | Vogt et al. |
| 6,610,383 B1 | 8/2003 | Morman et al. |
| 6,623,465 B1 | 9/2003 | Roe et al. |
| 6,632,212 B1 | 10/2003 | Morman et al. |
| 6,645,190 B1 | 11/2003 | Olson et al. |
| 6,679,869 B1 | 1/2004 | Schlinz et al. |
| 6,682,512 B2 | 1/2004 | Uitenbroek et al. |
| 6,685,688 B2 | 2/2004 | Mishima et al. |
| 6,702,799 B2 | 3/2004 | Otsubo |
| 6,702,800 B1 | 3/2004 | Vukos et al. |
| 6,703,538 B2 | 3/2004 | Lassen et al. |
| 6,706,028 B2 | 3/2004 | Roe et al. |
| 6,755,808 B2 | 6/2004 | Balogh et al. |
| 6,869,424 B1 | 3/2005 | Morman et al. |
| 6,881,205 B2 | 4/2005 | Zehner et al. |
| 6,969,378 B1 * | 11/2005 | Vukos et al. ............. 604/385.22 |
| 2002/0103470 A1 | 8/2002 | Molander et al. |
| 2002/0104608 A1 | 8/2002 | Welch et al. |
| 2002/0165516 A1 | 11/2002 | Datta et al. |
| 2002/0188268 A1 | 12/2002 | Kline et al. |
| 2003/0023213 A1 | 1/2003 | Fernfors et al. |
| 2003/0083635 A1 | 5/2003 | Gibbs |
| 2003/0120243 A1 * | 6/2003 | Uitenbroek et al. ...... 604/385.16 |
| 2003/0125696 A1 | 7/2003 | Morman et al. |
| 2003/0208171 A1 | 11/2003 | Zehner et al. |
| 2004/0013850 A1 | 1/2004 | Kling |
| 2004/0044323 A1 | 3/2004 | Roessler et al. |
| 2004/0102749 A1 | 5/2004 | Olson et al. |
| 2004/0127878 A1 | 7/2004 | Olson et al. |
| 2004/0127881 A1 | 7/2004 | Stevens et al. |
| 2004/0181200 A1 | 9/2004 | Desai et al. |
| 2004/0193133 A1 | 9/2004 | Desai et al. |
| 2005/0124961 A1 | 6/2005 | Morman et al. |
| 2006/0004342 A1 | 1/2006 | Sawyer et al. |
| 2006/0035055 A1 | 2/2006 | Schneider et al. |

FOREIGN PATENT DOCUMENTS

| | | |
|---|---|---|
| EP | 0 904 756 B1 | 3/2004 |
| EP | 1 402 867 A2 | 3/2004 |
| GB | 2 284 538 A | 6/1995 |
| GB | 2 305 610 A | 4/1997 |
| GB | 2 310 606 A | 9/1997 |
| GB | 2 325 146 A | 11/1998 |
| JP | 60-194947 A | 10/1985 |
| WO | WO 93/06805 A1 | 4/1993 |
| WO | WO 95/19753 A1 | 7/1995 |
| WO | WO 97/23186 A1 | 7/1997 |
| WO | WO 98/52506 A1 | 11/1998 |
| WO | WO 99/58092 A1 | 11/1999 |

| | | |
|---|---|---|
| WO | WO 00/37009 A2 | 6/2000 |
| WO | WO 01/88245 A2 | 11/2001 |
| WO | WO 02/34184 A1 | 5/2002 |
| WO | WO 03/051254 | 6/2003 |
| WO | WO 03/057106 A1 | 7/2003 |
| WO | WO 2004/006817 A1 | 1/2004 |
| WO | WO 2004/020174 A1 | 3/2004 |
| WO | WO 2004/108041 A1 | 12/2004 |

OTHER PUBLICATIONS

"Polyethylene—Low Density (LDPE)—Material Information," Internet web page "http://www.goodfellow.com/csp/active/STATIC/E/Polyethylene_-_Low_Density.HTML", Goodfellow Corporation, Devon, PA, viewed and printed Jul. 5, 2005, pp. 1-4.

* cited by examiner

ABSORBENT GARMENTS WITH MULTIPART LINER HAVING VARIED STRETCH PROPERTIES

BACKGROUND OF THE INVENTION

Absorbent articles such as diapers, training pants, incontinence garments, swim undergarments, and the like conventionally include a liquid permeable body-facing liner, a liquid impermeable outer cover, and an absorbent core. The absorbent core is typically located in between the outer cover and the liner for taking in and retaining liquids (e.g., urine) exuded by the wearer.

In some of these absorbent articles, the articles contain various elastic materials to permit some expansion of the article when necessary to provide a better fit on the wearer. The elastic members are also designed to contract when being worn in order to provide the article with form-fitting properties at least in some areas. During use, the article is subjected to forces such as those generated by loading of the absorbent article and movement of the wearer. In some instances, after the absorbent article has been insulted with a liquid, the crotch area of the article may begin to droop or sag.

In this regard, improvements are needed in constructing absorbent articles that have form-fitting properties, even after the article has absorbed substantial amounts of liquid. In particular, a need exists for an absorbent article that does not droop or sag in the crotch area after being wetted. A need also exists for an absorbent article that has improved donning characteristics.

SUMMARY OF THE INVENTION

In general, the present invention relates to disposable absorbent articles having carefully controlled stretch properties. For instance, the absorbent articles may have form-fitting properties resulting in an improved fit and appearance. The carefully controlled stretch properties of the articles prevent against sagging or drooping in the crotch region, even after the article has been wetted. Specifically, the crotch region is prevented from drooping in the crotch region as the article receives bodily exudates.

For example, in one aspect of the invention, an absorbent article includes an outer cover made from a stretchable material; a stretchable bodyside liner joined to the outer cover in a superimposed relation; and an absorbent structure positioned in between the outer cover and the liner. The outer cover, liner and absorbent structure together form a chassis having a longitudinal axis and a lateral axis. The liner includes three zones across a lateral direction, the three zones comprising a first edge zone, a middle zone, and a second edge zone. The middle zone is a uniaxial stretch material that stretches in a first direction, and the respective first and second edge zones stretch in a second direction that is different than the first direction.

In another aspect of the present invention, an absorbent article includes an outer cover with a stretchable material and a stretchable bodyside liner joined to the outer cover in a superimposed relation; and an absorbent structure positioned in between the outer cover and the liner. The outer cover, liner and absorbent structure form a chassis having a longitudinal axis and a lateral axis. The liner has three zones across a lateral direction, the three zones including a first edge zone, a middle zone, and a second edge zone. The middle zone is substantially limited to stretching in a direction parallel to the lateral axis, and the respective first and second edge zones can stretch in a direction that is not parallel to the lateral axis.

In yet another aspect of the invention, a disposable absorbent article has an outer cover and a stretchable bodyside liner joined to the outer cover in a superimposed relation. The outer cover and liner form a chassis having a longitudinal axis and a lateral axis. The liner comprises three zones across a lateral direction, the three zones comprising a first edge zone, a middle zone having opposite longitudinal sides, and a second edge zone. The middle zone is substantially limited to stretching in a direction parallel to the lateral axis, and the respective first and second edge zone can stretch in multiple directions.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
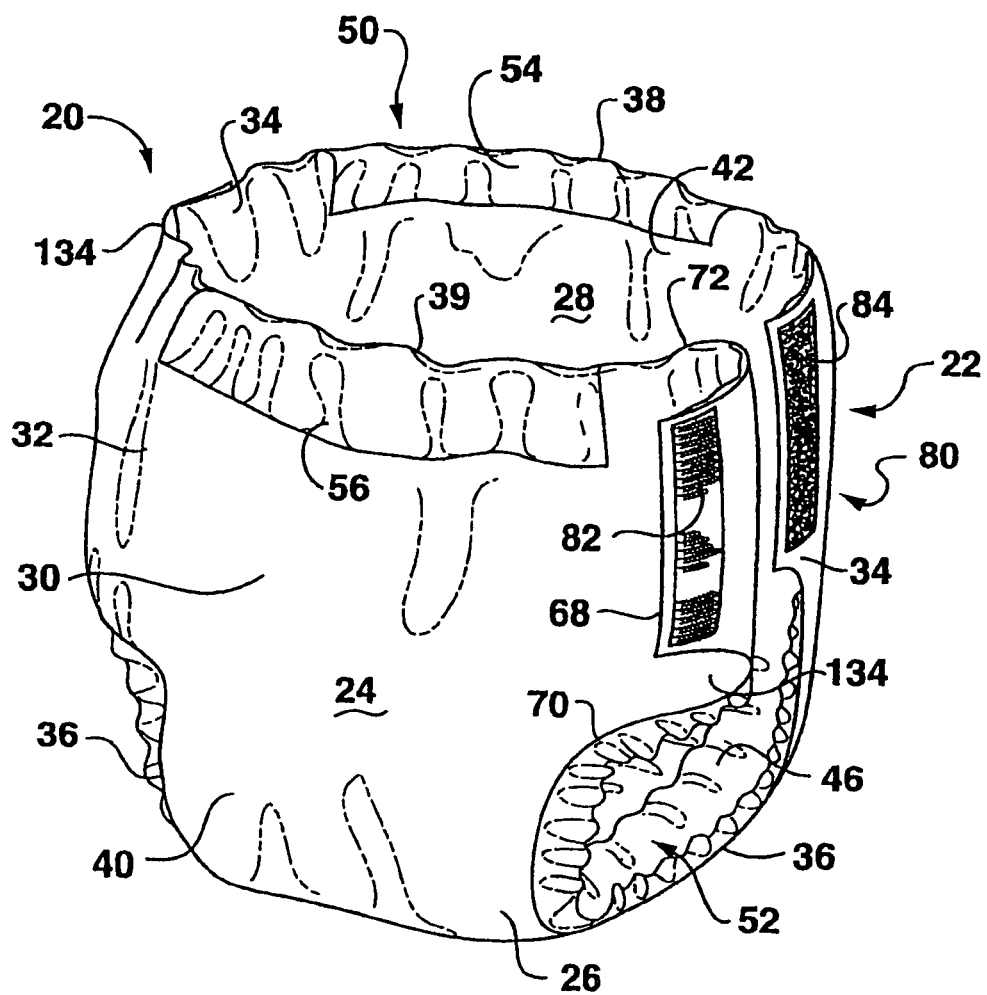
FIG. 1 is a perspective view of one embodiment of an absorbent article made in accordance with the present invention.

Repeated use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

In general, the present invention is directed to absorbent articles designed to provide improved dry and wet fit while also providing improved ease of manufacture. The absorbent article may be, for instance, a diaper, a toilet training pant, an adult incontinence garment, a swim pant, or the like. Absorbent garments made according to the present invention have stretch in at least one dimension. At least one of the stretch zones may exhibit biaxial or multi-axial stretch properties. In particular, the absorbent articles of the present invention have a central stretch zone with uniaxial stretch properties at least in the lateral or longitudinal direction, and side stretch zones that stretch in a different uniaxial direction, and/or exhibit biaxial or multi-axial stretch properties.

Through the above carefully controlled stretch-direction properties, the present inventors have found that absorbent articles exhibit improved fit and appearance. In particular, areas with specific stretch direction provides form-fitting properties while also preventing sagging or drooping of the crotch region, even after the crotch region is wetted. In particular, the construction of the absorbent article maintains the article in close contact with the body, even after the article is insulted with a liquid. The construction of the article further allows for a product that fits well yet is easier to manufacture and less expensive than an all-over stretch product.

In general, the absorbent articles are made with stretchable and/or elastic materials. As used herein, the term "stretchable" refers to a material that may be extended, deformed or the like, without breaking, and may or may not significantly retract after removal of an extending force. The stretchable material may extend with or without recovery. The terms "elastic" or "elastomeric" are used interchangeably herein and refer to a property of a material where upon removal of an elongating force, the material is capable of recovering a significant percent, suitably at least about 50 percent of the original dimension of its unstretched size and shape. In particular, elastic materials utilized in connection with the present invention may be elongated/extended or stretched in at least one direction without breaking by at least 15 percent, such as by at least 25 percent (to at least 125 percent of its initial unstretched length) in at least one direction, suitably by at least 50 percent (to at least 150 percent of its initial unstretched length). It is generally advantageous that the elastomeric material or composite be capable of being elongated by at least 100 percent, more desirably at least 200 percent, of its relaxed length and recover at least 30 percent and more desirably 50 percent of its elongation upon release of a stretching, biasing force, within about one minute.

Referring to FIG. 1, for exemplary purposes, an absorbent article such as training pants 20 that may be made in accordance with the present invention is shown. The pants 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, other personal care or health care garments, and the like without departing from the scope of the present invention.

By way of illustration only, various materials and methods for constructing training pants 20 of the various aspects of the present invention are disclosed in the following commonly owned patents and applications: PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al.; and U.S. Ser. No. 10/881,718 to Sawyer et al. which are incorporated herein by reference to the extent they are consistent (i.e., not in conflict) herewith.

Figure 2:
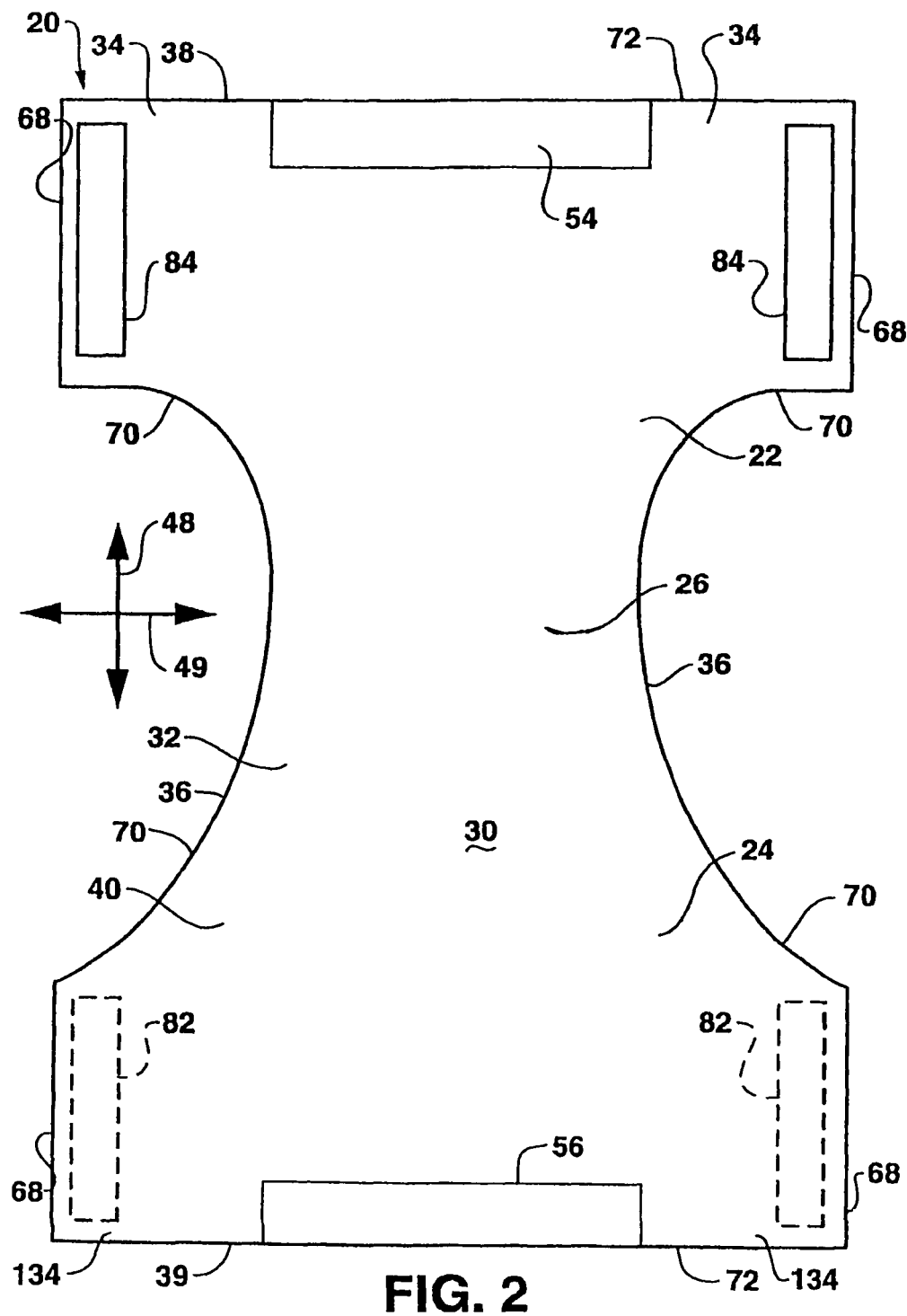
FIG. 2 is a plan view of the absorbent article shown in FIG. 1 with the article in an unfastened, unfolded and laid flat condition showing the surface of the article that faces away from the wearer.
Figure 3:
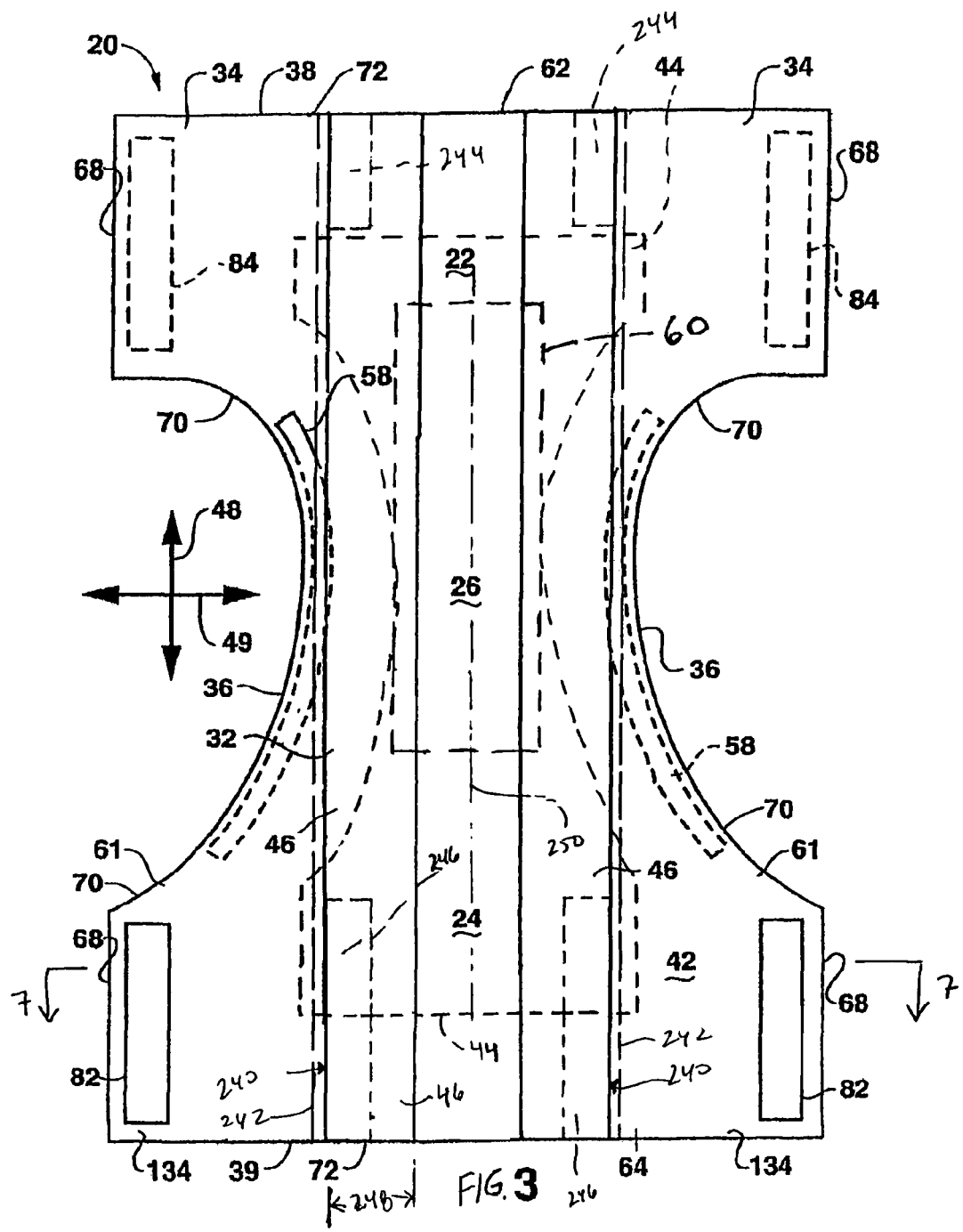
FIG. 3 is a plan view similar to FIG. 2 showing the surface of the absorbent article that faces the wearer when worn and with portions cut away to show underlying features.

A pair of training pants 20 is representatively illustrated in FIG. 1 in a partially fastened condition. The training pants 20 shown in FIG. 1 is also represented in FIGS. 2 and 3 in an opened and unfolded state. Specifically, FIG. 2 is a plan view illustrating the exterior side of the pants 20, while FIG. 3 illustrates the interior side of the pants 20. As shown in FIGS. 2 and 3, the pants 20 defines a longitudinal direction 48 that extends from the front of the training pants when worn to the back of the training pants. Opposite to the longitudinal direction 48 is a lateral direction 49.

The pants 20 includes a chassis 32 defining a pair of longitudinal end regions, otherwise referred to herein as a front region 22 and a back region 24, and a center region, otherwise referred to herein as a crotch region 26, extending longitudinally between and interconnecting the front and back regions 22, 24. The pant 20 also defines an inner surface 28 adapted in use (e.g., positioned relative to the other components of the pants 20) to be disposed toward the wearer, and an outer surface 30 opposite the inner surface. The front and back regions 22, 24 are those portions of the pants 20, which when worn, wholly or partially cover or encircle the waist or midlower torso of the wearer. The crotch region 26 generally is that portion of the pants 20 which, when worn, is positioned between the legs of the wearer and covers the lower torso and crotch of the wearer. The training pants 20 have a pair of laterally opposite side edges 36 and a pair of longitudinally opposite waist edges, respectively designated front waist edge 38 and back waist edge 39.

As shown in FIGS. 1 through 3, pants 20 includes a pair of laterally opposite front side panels 34 extending laterally outward at the front region 22 and a pair of laterally opposite back side panels 134 extending laterally outward at the back region 24. The front side panels 34 and/or the back side panels 134 may be integral with the chassis 32 or may comprise separate components that are attached to the chassis. Pants 20 also may generally include an outer cover 40, a bodyside liner 42, and absorbent structure 44, flaps 46, fastening system 80, and waist (54,56) and leg (58) elastic members. Each of the pant 20 components maybe described herein as follows.

The side panels 34 and 134 can be formed as an integral portion of the chassis 32, and be formed in part by the liner 42. For example, the side panels 34, 134 can include a generally wider portion of the outer cover 40, the bodyside liner 42, and/or other components of the chassis 32. As described above, the side panels 34 and 134 may be attached together using any suitable fastening system 80.

In the embodiments shown in the figures, the side panels 34 and 134 are releasably attachable. It should be understood, however, that in other embodiments the side panels 34 and 134 may be permanently joined together. For instance, the side panels may be made from a unitary piece of material. Alternatively, the side panels may be bonded together using ultrasonic bonding, thermal bonding or an adhesive. In this embodiment, the absorbent article is pulled over the legs when being worn.

Figure 5:
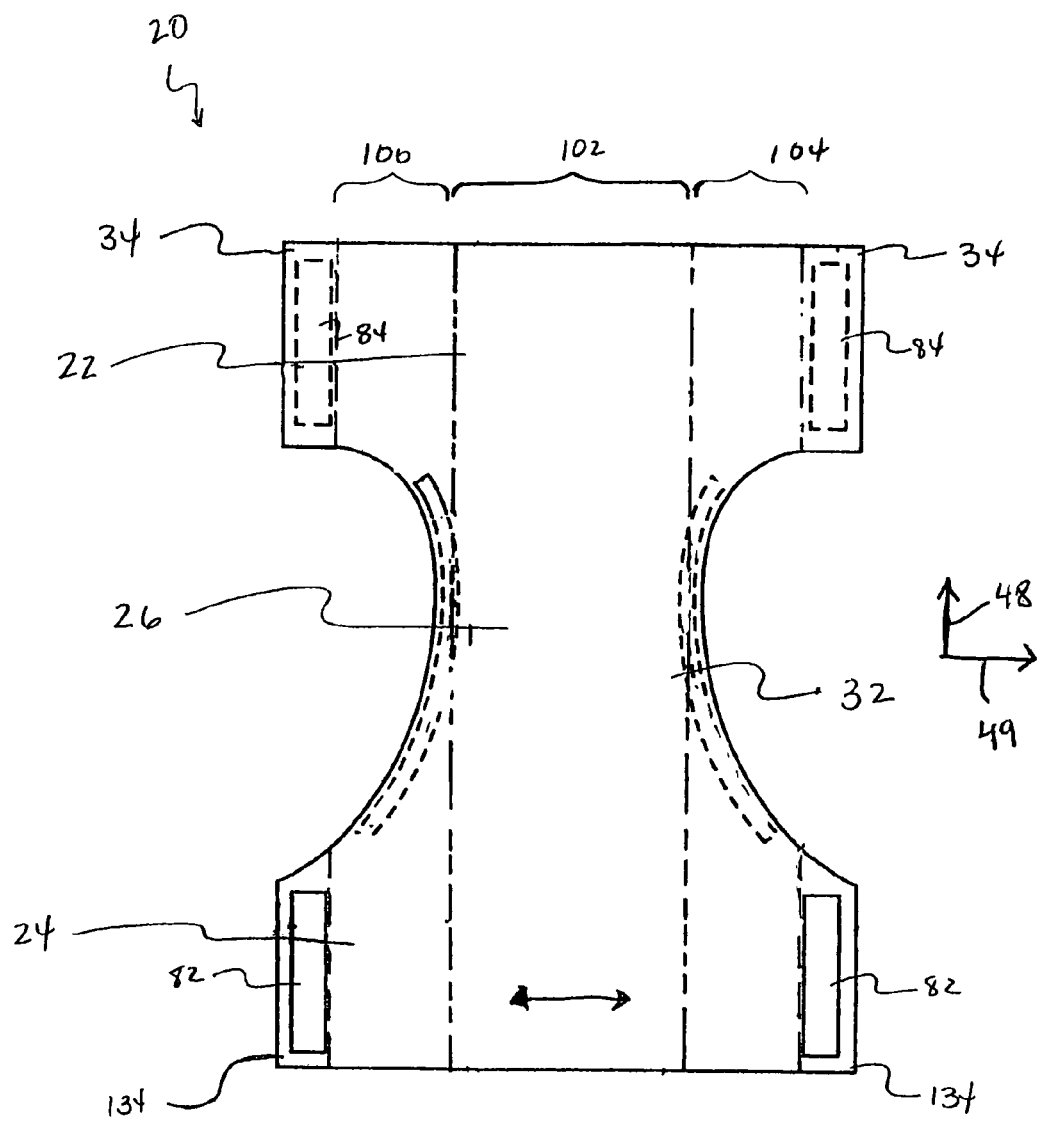
FIG. 5 is a simplified plan view of another embodiment of an absorbent article made in accordance with the present invention showing the stretch properties of the liner.
Figure 6:
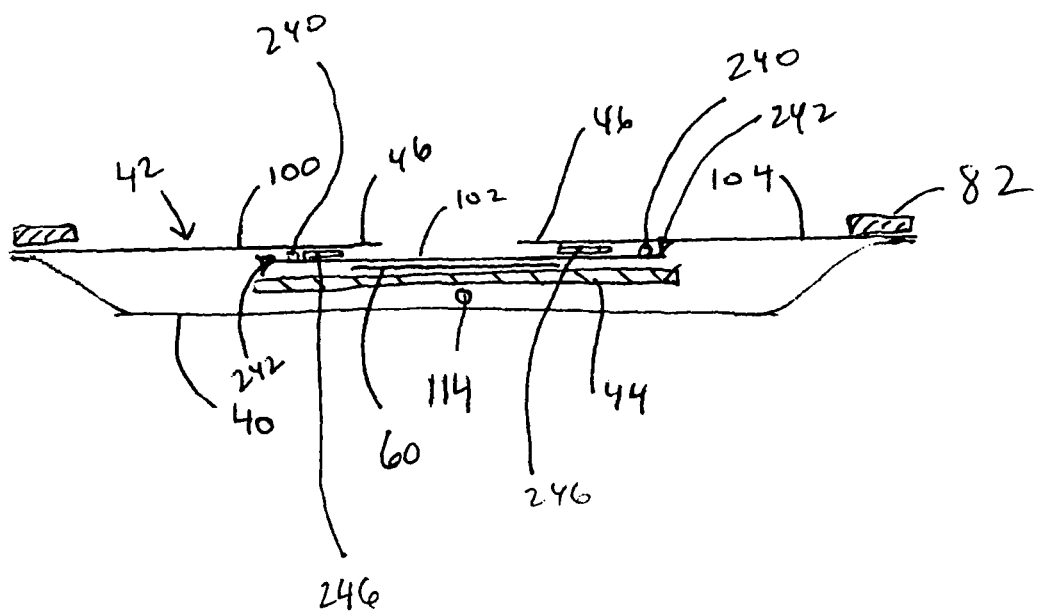
FIG. 6 is a cross-sectional side elevation of the article shown in FIG. 3, taken at line 7-7.

In an alternative embodiment of the present invention, the side panels 34 and 134 may be separately attached to the chassis 32 as shown in FIG. 5. Unlike side panels formed form a liner 42, where it is possible that bodily exudates could make contact with any portion of the liner 42, the separately attached side panels are not meant to receive, absorb or make contact with bodily exudates. However, such contact could be made inadvertently. The separate front side panels 34 can be permanently bonded to and extend transversely outward beyond the side margins of the chassis 32. Similarly, the back side panels 134 can be permanently bonded to and extend transversely outward beyond the side margins of the chassis 32 and the back region 24. The side panels 34 and 134 may be bonded to the chassis 32 using attachment means known to those skilled in the art such as adhesive, thermal or ultrasonic bonding.

The front and back side panels 34 and 134 each have a longitudinal outer edge 68, and a leg end edge 70 disposed toward the longitudinal center of the training pants 20, and waist end edges 72 disposed toward a longitudinal end of the training pants. The leg end edges 70 and the outer edges 68 of the side panels 34 and 134 form part of the pant side edges 36 of the training pants 20. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. The waist end edges 72 are suitably parallel to the transverse axis 49. The waist end edges 72 of the front side panels 34 form part of the front waist edge 38 of the training pants 20, and the waist end edges 72 of the back side panels 134 form part of the back waist edge 39 of the pants.

In configurations where the side panels 34, 134 are separately attached as shown in FIG. 5, the side panels may be provided by an elastic material capable of stretching at least in a direction generally parallel to the lateral direction 49 of the training pants 20. Suitable elastic materials, as well as one process of incorporating elastic side panels into training pants, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; U.S. Pat. No. 4,720,415 issued Jan. 19, 1988 in the name of Taylor et al.; and PCT application WO 01/88245 in the name of Welch et al.; all of which are incorporated herein by reference to the extent that they are consistent (i.e., not in conflict) herewith. Alternatively, the side panel material may include other woven or non-woven materials, such as those described later herein as being suitable for construction of the outer cover 40 and/or the bodyside liner 42; mechanically pre-strained composites; or stretchable but inelastic materials.

Referring to FIGS. 1-3, the chassis 32 includes an outer cover 40 and a multi-part bodyside liner 42 that may be joined to the outer cover 40 in a superimposed relation therewith by adhesives, ultrasonic bonds, thermal bonds or other conventional techniques. Referring to FIG. 3, the liner 42 may suitably be joined to the outer cover 40 along the perimeter of the chassis 32 to form a front waist seam 62 and a back waist seam 64. As shown in FIG. 3, the liner 42 may suitably be joined to the outer cover 40 to form a pair of side seams 61 in the front region 22 and the back region 24. The liner 42 can be generally adapted, i.e., positioned relative to the other components of the pants 20, to be disposed toward the wearer's skin during wear of the pants.

Figure 4:
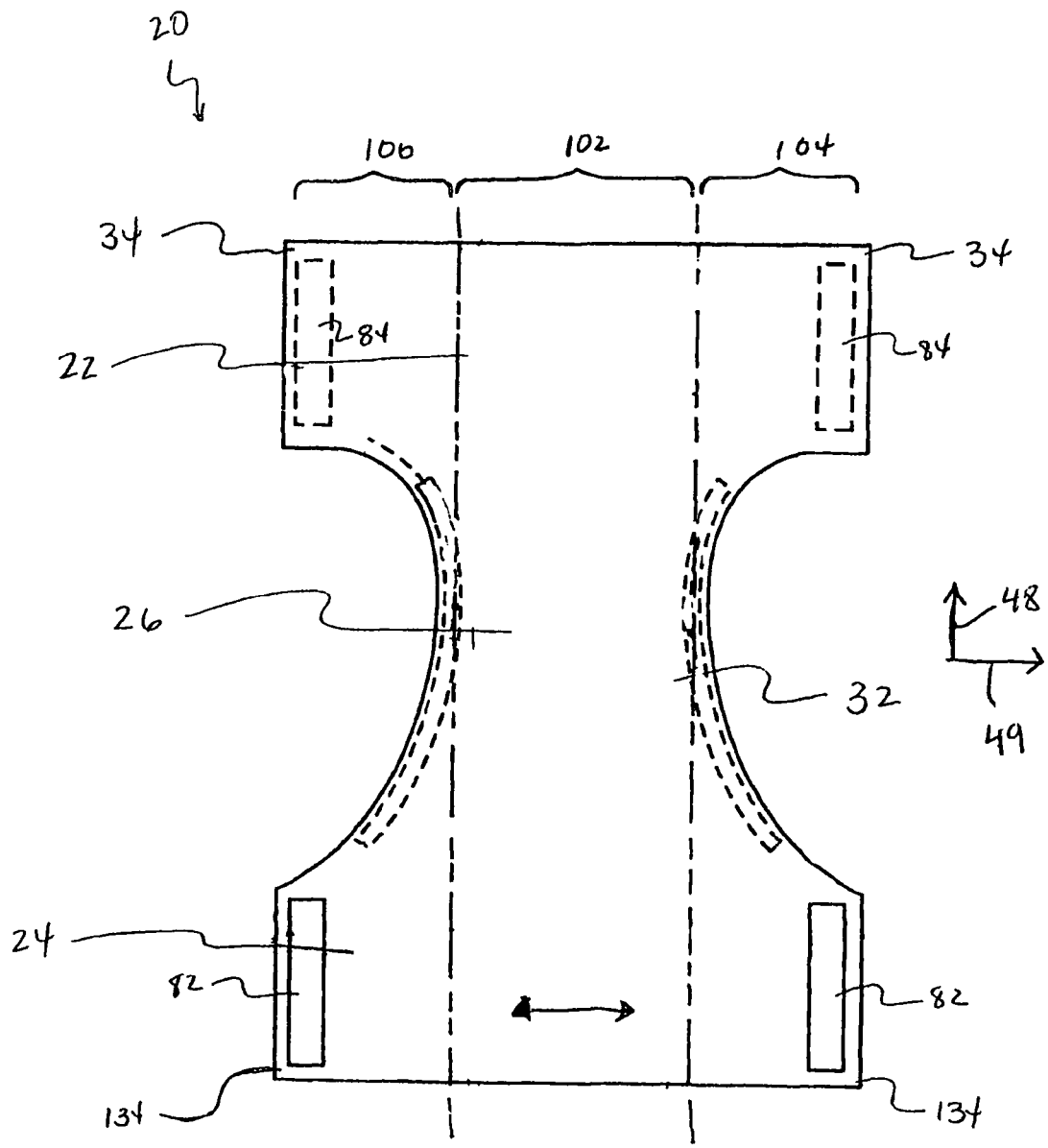
FIG. 4 is a simplified plan view of the absorbent article shown in FIG. 3 illustrating the stretch properties of the liner.

As described above, the multi-part bodyside liner 42 of the present invention is particularly directed to absorbent articles different stretch directions in select zones. Referring to FIG. 4, the absorbent article 20 is shown in a flat state containing diagrammatical arrows illustrating one embodiment of a pant with the stretch directions in each portion of the liner 42. As illustrated, the liner 42 of the pant 20 for purposes of explanation is partitioned into at least three zones. The zones include a first edge zone 100, a middle zone 102, and a second edge zone 104.

The direction of stretch contained in the middle zone varies from the direction of stretch in the edge zones depending upon the particular circumstances and the desired result. Most suitably, in some embodiments of the present invention the middle zone 102 stretches only in the lateral direction 49, and the edge zones 100, 104 stretch in a biaxial, multiaxial or longitudinal direction. In another embodiment, the middle zone 102 stretches only in the longitudinal direction 48, and the edge zones 100, 104 stretch in a biaxial, multiaxial or lateral direction 49. As used herein, the term "biaxial" is defined as a stretchable material that can stretch in more than one direction, yet exhibits more stretch in one direction than another. Biaxial stretch materials can stretch in more than two directions. The term "multiaxial" is defined as a stretchable material that can stretch in more than one direction, yet does not exhibit more stretch in one direction than another.

In one embodiment of the present invention, the edge zones 100, 104 may exhibit the most stretch biaxially in directions 48, 49, the longitudinal and lateral directions, respectively. One skilled in the art will realize that all other orientations of the biaxial material are possible. As disclosed in previously incorporated patent application U.S. Ser. No. 10/881,718, the edge zones may have different percentages of stretch than the middle zone.

Through the above construction, the pant 20 is provided with form-fitting properties that not only maximize comfort but also provide an aesthetically pleasing appearance when worn. The use of different materials with different stretch properties in various zones, for instance, maintains the crotch region next to the wearer, even after the absorbent garment has been wetted. Moreover, the product is more economical to produce if a portion of the liner contains a lesser-expensive material that is limited to stretch in a single direction. Another benefit is in processing; it is far easier to utilize a material that is not 100 percent biaxial. In particular, if the liner 42 is formed from biaxial-stretch edge zones and a lateral-stretch middle zone, then the overall liner can more easily handled during processing because it will not stretch in the machine direction (in an MD oriented pant process).

It should be understood that the above stretch properties of absorbent articles made in accordance with the present invention are contained solely in the liner 42 in the lateral direction. As used herein, the stretch properties of the liner are independent of the properties of any auxiliary components, such as flap elastics, waist elastic members, elastic gasket components, or leg elastic components.

For instance, referring to FIG. 5, when the front side panels 34 and the back side panels 134 are not integral with the chassis 32, the liner 42 edge zones 100 and 104 and the middle zone 102 are independent of the front and back side panels. As shown in FIG. 5, for instance, the chassis 32 has been divided into three zones 100, 102 and 104 that possess the stretch properties described above. The side panels 134, 34 may or may not have stretch properties.

Elasticized containment flaps 46 as shown in FIG. 3 define a partially unattached edge which assumes an upright configuration in at least the crotch region 26 of the training pants 20 to form a seal against the wearer's body. The containment flaps 46 can extend longitudinally along the entire length of the chassis 32 or may extend only partially along the length of the chassis. Suitably, flaps 46 are constructed from the middle or edge zones of the liner 42, but may be formed from separate materials. Referring to FIGS. 3 and 7, flaps 46 are sealed by a flap seaming bead 240, which extends the entire length of the flap 46, adjacent side edges 242 of middle zone 102. Flap seaming bead may be adhesive, a pressure bond, thermal bond, ultrasonic bonds, or combinations thereof.

At each waist region, flaps 46 are fixed to the middle zone 102 so that the flap stays flat in front and rear waist regions 22 and 24. Flaps 46 are fixed with an area of adhesive or other bonding methods or materials as disclosed herein, the area being referred to as a dead zone because it does not significantly limit the amount of stretch. In both waist regions, each dead zone 244 and 246 extends from the flap bead 240 to about half the width 248 of flap 46. In the front waist region 24, dead zones 244 extend inboard from edge 38 until it reaches absorbent element 44. In the rear waist region 24, dead zones 246 extend inboard from edge 39 and overlaps absorbent element 44. Dead zones 246 extend inboard to about the length of longitudinal outer edge 68. In the alternative, not shown, each dead zone in the front or rear waist region may extend fully across the width 248 of flap 46.

Suitable constructions and arrangements for the containment flaps 46 are generally well known to those skilled in the art and are described in U.S. Pat. No. 4,704,116 issued Nov. 3, 1987 to Enloe, which is incorporated herein by reference.

Positioned in between the outer cover 40 and the liner 42 is a substantially nonelastic absorbent structure 44 for absorbing liquid body exudates exuded by the wearer. The absorbent structure 44 is shown attached to the outer cover 40 using, for instance, an adhesive 114. By attaching the absorbent structure 44 to the outer cover 40, the stretch properties of the outer cover 40 and liner 42 are not significantly inhibited, especially in the middle zone 102. In accordance with the present invention, the adhesive 114 may be applied as a bead 250. As seen in FIGS. 3 and 7, bead 250 extends the length of the absorbent structure 44 because in this particular embodiment, the middle zone 102 is only stretchable in the lateral direction 49. In the alternative, a pair of spaced beads of adhesive oriented in the longitudinal direction 49 if the middle zone 102 is limited in stretch to the machine direction. Of course, patterns of adhesive could be used as is known in the art.

The adhesive 114 used to construct the absorbent article 20 may be any suitable adhesive for the application. For instance, in one embodiment, a hot melt adhesive may be used. The hot melt adhesive may be, for instance, any suitable adhesive such as FINDLEY H-2096 or H-2525A adhesive commercially available from Bostik Findley Adhesives, Inc.

In addition to using an adhesive, various other attachment devices may be used in order to attach the absorbent structure 44 to the outer cover 40 and/or to the liner 42. For instance, in other embodiments, the absorbent structure may be ultrasonically bonded to the chassis 32, thermally bonded to the chassis 32, or bonded using heat crimping. In other embodiments, a mechanical attachment structure such as a hook and loop fastening system may be used in order to secure the absorbent structure to the chassis.

The absorbent article 20 may further include a surge management layer 60 (see FIG. 1) which may be optionally located adjacent the absorbent structure 44 and attached to various components in the article 20 such as the absorbent structure 44 or the bodyside liner 42 by methods known in the art, such as by using an adhesive. As further described herein, surge management layer is attached to pant 20 in such a manner as to not prohibit stretch where stretch is desired. A surge management layer 60 helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management materials are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

With the training pants 20 in the fastened position as partially illustrated in FIG. 1, the front and back side panels 34, 134 can be connected together by a fastening system 80 to define a three-dimensional pants configuration having a waist opening 50 and a pair of leg openings 52. The front and back side panels 34 and 134, upon wearing of the pants 20, thus include the portions of the training pants 20 which are positioned on the hips of the wearer. The waist edges 38 and 39 of the training pants 20 are configured to encircle the waist of the wearer and together define a waist opening 50 of the pants.

The fastening system 80 may include laterally opposite first fastening components 82 adapted for refastenable engagement to corresponding second fastening components 84. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include loop fasteners and the second fastening components 84 include complementary hook fasteners. Alternatively, the first fastening components 82 may include hook fasteners and the second fastening components 84 may be complementary loop fasteners. In another aspect, the fastening components 82, 84 can be interlocking similar surface fasteners, or adhesive and cohesive fastening elements such as an adhesive fastener and an adhesive-receptive landing zone or material; or the like. Although the training pants 20 illustrated in FIG. 1 indicate the back side panels 134 overlapping the front side panels 34 upon connection thereto, which is convenient, the training pants 20 can also be configured so that the front side panels 34 overlap the back side panels 134 when connected. One skilled in the art will recognize that the shape, density and polymer composition of the hooks and loops may be selected to obtain the desired level of engagement between the fastening components 82, 84. Optionally, either one or both of the fastening components 82, 84 may be provided by one of the inner or outer surfaces 28 and 30 of the side panels 34 and 134. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

To further enhance containment and/or absorption of body exudates, the training pants 20 may also suitably include a front waist elastic member 54 (FIG. 1), a rear waist elastic member 56, and leg elastic members 58 (FIG. 3), as are known to those skilled in the art. The waist elastic members 54 and 56 can be operatively joined to the outer cover 40 and/or the bodyside liner 42 and can extend over part or all of the waist edges 38, 39. The waist elastic members 54 and 56 may comprise a single piece of elastic material or may comprise a plurality of individual components that are either connected together or spaced apart from each other. The leg elastic members 58 can be operatively joined to the outer cover 40 and/or the bodyside liner 42 and positioned in the crotch region 26 of the training pants 20.

The waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

Various techniques may be used in order to produce the absorbent article 20 with the above stretch-direction properties. In constructing absorbent articles in accordance with the present invention, for instance, the outer cover 40 may be elastic, while the bodyside liner 42 is stretchable or vice versus. In other embodiments, both the outer cover and the bodyside liner may be elastic. Depending upon the construction of the article, the absorbent structure 44 may also be stretchable and/or elastic.

In one particular embodiment, the outer cover 40 and/or the bodyside liner 42 are made from stretchable and/or elastic materials. These materials are incorporated into the pant 20 in a manner that provides the article with stretch characteristics in the lateral direction.

As mentioned, the outer cover 40, the bodyside liner 42 and/or the absorbent structure 44 is formed from multiple components and separate pieces that are attached together to form the absorbent article 20 having the desired stretch properties. For instance, two pieces of material may be used, to construct the edge zones 100 and 104. These pieces of material may be stretchable and/or elastic in a direction that is different from the middle zone 102 of the chassis 32. The three pieces of material may then be connected or attached together using any suitable attachment technique, such as thermal bonding, pressure bonding or the like, or through the use of an adhesive. In this embodiment, the outer cover, the liner or both the outer cover and the liner may be made from three separate pieces of material that assist in creating the desired stretch characteristics.

The outer cover 40, the inner liner 42 and the absorbent structure 44 may be made from many different materials depending upon the particular application and the desired result. All three layers, for instance, may be stretchable and/or elastic.

The outer cover 40 may be made from various materials. The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, pressure bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The outer cover 40 is stretchable and optionally elastic. Elastic non-woven laminate webs that can be used as the outer cover 40 include a non-woven material joined to one or more gatherable non-woven webs, films, or foams. Stretch Bonded Laminates (SBL) and Neck Bonded Laminates (NBL) are examples of elastomeric composites. Non-woven fabrics are any web of material which has been formed without the use of textile weaving processes which produce a structure of individual fibers that are interconnected in an integrating manner.

Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films, foams, meltblown fabrics or spunbond fabrics composed of polyethylene, polypropylene, or polyolefin elastomers, as well as combinations thereof. The elastomeric materials may include PEBAX elastomer (available from AtoChem located in Philadelphia, Pa.), HYTREL elastomeric polyester (available from Invista of Wilmington, Del.), KRATON elastomer (available from Kraton Polymers of Houston, Tex.), or strands of LYCRA elastomer (available from Invista of Wilmington, Del.), or the like, as well as combinations thereof. The outer cover 40 may include materials that have elastomeric properties through a mechanical process, printing process, heating process, or chemical treatment. For examples such materials may be apertured, creped, neck-stretched, heat activated, grooved, embossed, and micro-strained; and may be in the form of films, webs, and laminates.

Suitable materials for a biaxially stretchable outer cover 40 include biaxially stretchable material and biaxially elastic stretchable material. One example of a suitable outer cover material can include a 0.3 osy (10.2 gsm) polypropylene spunbond that is necked 60 percent in the lateral direction 49 and creped 60 percent in the longitudinal direction 48, laminated with 3 grams per square meter (gsm) Findley 2525A styrene-isoprene-styrene based adhesive to 8 gsm PEBAX 2533 film with 20 percent $TiO_2$ concentrate.

Another example of a suitable material for a biaxially stretchable outer cover 40 is a breathable elastic film/nonwoven laminate, described in U.S. Pat. No. 5,883,028, issued to Morman et al., incorporated herein by reference to the extent that it is consistent (i.e. not in conflict) herewith. Examples of materials having two-way stretchability and retractability are disclosed in U.S. Pat. No. 5,116,662 issued to Morman and U.S. Pat. No. 5,114,781 issued to Morman, both of which are hereby incorporated herein by reference to the extent that it is consistent (i.e., not in conflict) herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The bodyside liner 42 may also be stretchable, and more suitably it may be elastomeric. Suitable elastomeric materials for construction of the bodyside liner 42 can include elastic strands, LYCRA elastics, cast or blown elastic films, non-woven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers.

As an additional example, in one aspect the bodyside liner 42 suitably includes a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) are adhered to the necked spunbond material. The fabric is surface treated with an operative amount of surfactant, such as about 0.6 percent AHCOVEL Base N62 surfactant, available from ICI Americas, a business having offices in Wilmington, Del., U.S.A. The surfactant can be applied by any conventional means, such as spraying, printing, brush coating or the like. Other suitable materials may be stretchable biaxially stretchable materials, such as a neck stretched/creped spunbond. The bodyside liner 42 can also be made from stretchable materials as are described in U.S. patent application Ser. No. 09/563,417 filed on May 3, 2000 by Roessler et al. The bodyside liner 42 can also be made from biaxially stretchable materials as are described in U.S. patent application Ser. No. 09/698,517 filed on Oct. 27, 2000 by Vukos et al.

In order to make the outer cover 40 and/or the liner 42 more stretchable or in order to otherwise control the stretch properties of the outer cover or liner, the materials may be perforated. The elastic side panels may also be perforated in order to increase the stretch characteristics. The perforations formed into the materials may be in any suitable shape, such as slits or holes.

The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394, and Favor 9543 superabsorbents are available from DeGussa Superabsorbers.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. Nos. 4,100,324 to Anderson, et al.; 5,284,703 to Everhart, et al.; and 5,350,624 to Georger, et al.; which are incorporated herein by reference to the extent they are consistent (i.e., not in conflict) herewith.

In a particular aspect of the absorbent article of the present invention, the absorbent structure 44 may also be elastomeric. For this purpose, the absorbent web material can include elastomeric fibers in an amount which is at least a minimum of about 2 wt percent. The amount of elastomeric fibers can alternatively be at least about 3 wt percent, and can optionally be at least about 5 wt percent to provide improved performance. In addition, the amount of elastomeric fibers can be not more than about 60 wt percent. Alternatively, the amount of elastomeric fibers can be not more than about 45 wt percent, and optionally, can be not more than about 30 wt percent to provide improved benefits. These values may impact the absorbent structure 44 by affecting the desired levels of stretchability and structural stability without excessively degrading the physical properties or the liquid-management properties of the absorbent structure. An absorbent web material with an excessively low proportion of elastomeric fibers may be insufficiently stretchable, and a web material with an excessively high proportion of elastomeric fibers may exhibit an excessive degradation of its absorbency functionalities, such as poor intake, poor distribution, poor retention of liquid.

The absorbent structure 44 may include an elastomeric coform absorbent web material. Such materials are described for instance in U.S. Pat. Nos. 6,231,557 and 6,362,389, which are each incorporated by reference herein to the extent they are consistent (i.e., not in conflict) herewith. In particular aspects, the elastomeric coform material can have an overall coform basis weight of at least about 50 gsm, such as up to about 1200 gsm. The coform basis weight, for example, may be at least about 100 gsm, such as at least about 200 gsm. These values can provide the absorbent structure with the desired stretchability and structural stability without excessively degrading the physical properties or the liquid-management functionalities of the absorbent structure. For example, retention portions having excessively low proportions of elastomeric coform material may not be sufficiently stretchable. Conversely, an absorbent web material having excessively large amounts of elastomeric coform materials can exhibit an excessive degradation of their absorbency functionalities, such as an excessive degradation of intake, distribution and/or retention properties.

Other examples of usable elastomeric absorbent bodies are described in international patent application WO 03/051254 and U.S. Pat. Nos. 5,964,743, 5,645,542, 6,231,557, and 6,362,389, each of which are incorporated by reference herein to the extent they are consistent (i.e., not in conflict) herewith.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article comprising:
   an outer cover comprising a stretchable material;
   a stretchable bodyside liner joined to the outer cover in a superimposed relation; and
   an absorbent structure positioned in between the outer cover and the liner;
   wherein the outer cover, liner and absorbent structure form a chassis having a longitudinal axis and a lateral axis, wherein the liner comprises three zones across a lateral direction, the three zones comprising a first edge zone, a middle zone, and a second edge zone, and wherein the middle zone is a uniaxial stretch material that stretches in a first direction, and the respective first and second edge zones stretch in a second direction that is different than the first direction and cannot stretch in the first direction.

2. The absorbent article of claim 1 wherein the respective first and second edge zones are biaxial.

3. The absorbent article of claim 1 the respective first and second edge zones are multiaxial.

4. The absorbent article of claim 1 wherein the uniaxial stretch material stretches substantially in the longitudinal direction.

5. The absorbent article of claim 1 wherein the uniaxial stretch material stretches substantially in the lateral direction.

6. The absorbent article of claim 5 wherein the outer cover is elastic.

7. The absorbent article of claim 5 wherein the liner is elastic.

8. The absorbent article of claim 5 wherein the absorbent structure is attached to the chassis by a longitudinally oriented bond.

9. The absorbent article of claim 1 wherein the outer cover comprises a biaxial material.

10. The absorbent article of claim 1 wherein the stretchable bodyside liner includes a first waist edge and a second waist edge, the second waist edge being opposite from the first waist edge, and wherein the first edge zone and the second edge zone extend substantially from the first waist edge to the second waist edge.

11. An absorbent article comprising:
    an outer cover comprising a stretchable material;
    a stretchable bodyside liner joined to the outer cover in a superimposed relation, the stretchable bodyside liner including a first waist edge and a second waist edge, the second waist edge being opposite from the first waist edge; and
    an absorbent structure positioned in between the outer cover and the liner;
    wherein the outer cover, liner and absorbent structure form a chassis having a longitudinal axis and a lateral axis, wherein the liner comprises three zones across a lateral direction, the three zones comprising a first edge zone, a middle zone, and a second edge zone, wherein the first edge zone and the second edge zone extend substantially from the first waist edge to the second waist edge, and wherein the middle zone is substantially limited to stretching in a direction parallel to the lateral axis, and the respective first and second edge zones can stretch in a direction that is not parallel to the lateral axis.

12. The absorbent article of claim 11 wherein the respective first and second edge zones are biaxial.

13. The absorbent article of claim 11 the respective first and second edge zones are multiaxial.

14. The absorbent article of claim 11 wherein the first edge zone and the second edge zone cannot stretch in the direction parallel to the lateral axis.

15. A disposable absorbent article comprising:
    an outer cover; and a stretchable bodyside liner joined to the outer cover in a superimposed relation;
wherein the outer cover and liner form a chassis having a longitudinal axis and a lateral axis, wherein the liner comprises three zones across a lateral direction, the three zones comprising a first edge zone, a middle zone having opposite longitudinal sides, and a second edge zone, and wherein the middle zone is substantially limited to stretching in a direction parallel to the lateral axis, and the respective first and second edge zone can stretch in multiple directions, the multiple directions not including the direction parallel to the lateral axis.

16. The disposable absorbent article of claim 15 wherein the outer cover is elastic.

17. The disposable absorbent article of claim 16 wherein the liner is elastic.

18. The disposable absorbent article of claim 15 further comprising a pair of flaps extending along each of the longitudinal sides of the middle zone.

19. The disposable absorbent article of claim 18 wherein the first edge zone and the second edge zone overlap the middle zone for forming the pair of flaps.

20. The disposable absorbent article of claim 15 wherein the outer cover is biaxially stretchable.

21. The disposable absorbent article of claim 20 further comprising a stretchable absorbent structure positioned in between the outer cover and the liner.

22. The disposable absorbent article of claim 21 wherein the absorbent structure is attached to the article by a bond oriented in the longitudinal direction.

23. The disposable absorbent article of claim 13 wherein the stretchable bodyside liner includes a first waist edge and a second waist edge, the second waist edge being opposite from the first waist edge, and wherein the first edge zone and the second edge zone extend substantially from the first waist edge to the second waist edge.

* * * * *